US009687449B2

(12) United States Patent
Harel (10) Patent No.: US 9,687,449 B2
(45) Date of Patent: Jun. 27, 2017

(54) NUTRACEUTICALS AND METHOD OF FEEDING AQUATIC ANIMALS

(75) Inventor: Moti Harel, Baltimore, MD (US)

(73) Assignee: Advanced Bionutrition Corp., Columbia, MD (US)

( * ) Notice: Subject to any disclaimer, the term of this patent is extended or adjusted under 35 U.S.C. 154(b) by 1106 days.

(21) Appl. No.: 10/534,090

(22) PCT Filed: Nov. 6, 2003

(86) PCT No.: PCT/US03/35250
§ 371 (c)(1), (2), (4) Date: Feb. 8, 2006

(87) PCT Pub. No.: WO2004/043140
PCT Pub. Date: May 27, 2004

(65) Prior Publication Data
US 2006/0127453 A1  Jun. 15, 2006

Related U.S. Application Data

(60) Provisional application No. 60/424,324, filed on Nov. 7, 2002.

(51) Int. Cl.

| A23K 1/165 | (2006.01) |
| A61K 9/16 | (2006.01) |
| A23K 40/20 | (2016.01) |
| A23K 40/30 | (2016.01) |
| A23K 10/18 | (2016.01) |
| A23K 20/163 | (2016.01) |
| A23K 20/195 | (2016.01) |
| A23K 50/40 | (2016.01) |
| A23K 50/80 | (2016.01) |

(52) U.S. Cl.
CPC ............ *A61K 9/1652* (2013.01); *A23K 10/18* (2016.05); *A23K 20/163* (2016.05); *A23K 20/195* (2016.05); *A23K 40/20* (2016.05); *A23K 40/30* (2016.05); *A23K 50/40* (2016.05); *A23K 50/80* (2016.05)

(58) Field of Classification Search
None
See application file for complete search history.

(56) References Cited

U.S. PATENT DOCUMENTS

| 4,076,846 A * | 2/1978 | Nakatsuka et al. ............ 426/62 |
| 4,239,754 A | 12/1980 | Sache et al. |
| 4,283,400 A * | 8/1981 | von Bittera et al. ......... 514/250 |
| 4,597,969 A | 7/1986 | Maxfield et al. |
| 5,149,799 A * | 9/1992 | Rubens ......................... 536/102 |
| 5,188,836 A | 2/1993 | Muhammad et al. |
| 5,229,131 A | 7/1993 | Amidon et al. |
| 5,362,424 A * | 11/1994 | Lee et al. ........................ 264/4.3 |
| 5,807,575 A * | 9/1998 | Dumoulin et al. ........... 424/464 |
| 6,017,388 A | 1/2000 | Yuan et al. |
| 6,190,591 B1 * | 2/2001 | van Lengerich .............. 264/141 |
| 6,228,419 B1 * | 5/2001 | Yuan .................... A23C 19/052 106/145.1 |
| 6,303,175 B1 * | 10/2001 | Kurzinger et al. ........... 426/573 |
| 6,340,527 B1 | 1/2002 | Van Soest et al. |
| 6,348,452 B1 | 2/2002 | Brown et al. |
| 6,375,985 B1 | 4/2002 | Bomberger et al. |
| 6,534,091 B1 | 3/2003 | Garces Garces et al. |
| 2003/0091630 A1 * | 5/2003 | Louie-Helm et al. ........ 424/468 |
| 2004/0047881 A1 | 3/2004 | Kyle et al. |
| 2004/0081638 A1 | 4/2004 | Kyle et al. |
| 2004/0177392 A1 | 9/2004 | Barratt et al. |
| 2006/0120999 A1 | 6/2006 | Dhar et al. |
| 2006/0121468 A1 | 6/2006 | Allnutt et al. |
| 2006/0130162 A1 | 6/2006 | Kyle et al. |
| 2006/0258623 A1 | 11/2006 | Harel et al. |
| 2006/0265766 A1 | 11/2006 | Kyle et al. |
| 2007/0082008 A1 | 4/2007 | Harel et al. |

FOREIGN PATENT DOCUMENTS

| EP | 0480729 | 4/1992 |
| EP | 0715484 | 6/1996 |
| JP | 08-089177 | 4/1996 |
| WO | WO87/01587 | 3/1987 |
| WO | WO 99/53902 | * 10/1999 ............... A61K 9/16 |
| WO | WO0032064 | * 6/2000 ............... A23P 1/04 |

(Continued)

OTHER PUBLICATIONS

Seib et al. in Location of amylose in normal starch granules. I. susceptibility of amylose and amylopectin to cross-linking reagents, Cereal Chem. 1992, vol. 69, pp. 405-409.*
Toshihisa et al., acid induced and calcium induced gelation of alginic acid: bead formation and pH-dependent swelling, chem. pharm. bull, 1991, vol. 39, pp. 1072-1074.*
Kailasapathy, Microencasulation of probiotic bacteria: technology and potential application, Curr. Issue Intest. Microbiol. 2002, vol. 3, pp. 39-48).*
Sultana et al. (Encapsulation of probiotic bacteria with alginate-starch and evaluation of survival in simulated gastrointestinal conditions and in yoghurt, Int. J. of Food Microbiology, 2000, pp. 47-55).*
Augsburger Ed. Pharmaceutical dosage forms: tablet, vol. 1, Informa Healthcare, New York 2008, Chapter 8, pp. 261-263.*
Dhar AK, Roux MM, Klimpel KR (2002) Quantitative assay for measuring the Taura syndrome virus and yellow head virus load in shrimp by real-time RT-PCR using SYBR Green chemistry. J. Virol. Methods 104: 69-82.

(Continued)

*Primary Examiner* — Bethany Barham
*Assistant Examiner* — Ping Cao
(74) *Attorney, Agent, or Firm* — RatnerPrestia (57) ABSTRACT

A delivery vehicle for bioactive agents and live probiotic microbes to aquatic animals protects the bioactive compounds and microbes from digestion and destruction in the animal stomach. It provides for controlled release of bioactive agents and live probiotic microbes to aquatic animals in the form of dry or wet beadlets with essential nutrients and attractants bound with soluble starch and cross-linked alginate. The bioactive agents and live probiotic microbes can be bound with emulsified high-amylose starch and embedded in the beadlets in the form of microparticles.

21 Claims, 4 Drawing Sheets

(56) References Cited

FOREIGN PATENT DOCUMENTS

WO     WO 02/00035    *   1/2002   ............. A23K 1/165
WO         03/018186        3/2003

OTHER PUBLICATIONS

Villamar DF, Langdon C (1993) Delivery of dietary components to larval shrimp (*Penaeus vannamei*) by means of complex microcapsules, Marine Biol. 115: 635-642.

European Examination Report dated May 8, 2015 in European Application No. 03789725.3.

* cited by examiner

Fig. 1

1.34 *L. rhamnosus* survival in Alginate/Starch Beads

Optimal Dosing of Probiotic is Important (Tilapia)

Fig. 4

Probiotic Effect on Shrimp Survival and FCR

Fig. 5

Effect of WSV Oral Challenge on WSV Titer in Probiotic Fed Shrimp

NUTRACEUTICALS AND METHOD OF FEEDING AQUATIC ANIMALS

PRIORITY CLAIM

This application claims the priority of provisional application 60/424,324 entitled "Nutraceuticals and Method of Feeding Aquatic Animals," filed in the United States Patent and Trademark Office on Nov. 7, 2002, the disclosure of which is hereby incorporated by reference in its entirety.

TECHNICAL FIELD

The invention relates to feeds for aquatic animals, delivery vehicles for bioactive agents to aquatic animals, and methods for providing the controlled release of bioactive agents, including probiotic microbes.

BACKGROUND ART

Conventional aquatic feeds are provided in dry, semi-dry, or wet forms. These feeds are either added directly to an aquaculture system or mixed with water prior to use. Conventional feeds rapidly deteriorate in water, with physical decomposition and breakdown of the feed starting immediately upon feed delivery into the culture water. Vulnerable bioactive agents start to decompose when the feed becomes soaked with water, and can then be destroyed by the animal's digestive processes. A barrier of particular significance in the design of feeds and feed additives in all vertebrates, including fish, is the gastrointestinal (GI) tract. Biological, chemical, and physical GI factors, such as varying pH in the GI tract, powerful digestive enzymes, and impermeable GI tract membranes, are all associated with the destruction of biologically or chemically active peptides and other components contained in feed or feed additives. Among the numerous agents which are not typically amenable to common oral administration methods are probiotic bacteria, hormones, polysaccharides, antibiotics, and other organic substances. These agents are rapidly rendered ineffective or are destroyed in the GI tract by acid hydrolysis, enzymes, or other catabolic processes unless adequately protected. A protective approach described in the literature involves coating or top-coating with semi-permeable materials for sustained release formulations (Muhammad et al. 1993). Another approach uses differential water solubility to deliver timed pulse delivery based on water solubility of the coating agents (Amidon and Leesman 1993).

One approach to overcoming some of the disadvantages associated with current feed delivery methods has been the development of microencapsulated diets. EP0237542 (Levine et al. 1987) describes a system where a nutritional component, such as a free amino acid or hormone (see, for example Sache and Bertrand, 1980), was entrapped in a liposome then further encapsulated in a hydrocolloid matrix. The resulting lipogel microcapsules were either stored as a freeze-dried powder or suspended in water containing chloramphenicol. Further, Villamar and Langdon, 1993 described the preparation of complex microcapsules consisting of dietary ingredients and lipid-wall microcapsules embedded in particles of a gelled mixture of alginate and gelatin to obtain a single type of food-particle used to provide suspension feeders with dietary nutrients.

It was also suggested, in WO 87/01587, that microcapsules using liposomes are useful for time-released delivery of materials such as drugs and hormones. These types of microcapsules are based upon phospholipids, which form a membrane around the medication and allow a time release of the medication through this membrane. This type of membrane barrier is fragile, expensive, and difficult to make, and not likely to remain as a discrete microcapsule when combined with other appropriate materials that would be part of a feed for marine animals. Moreover, liposomes are not capable of encapsulating significant amounts of bioactive nutrients.

The microencapsulated feeds described in the art do not solve all of the problems associated with conventional feeds. Production of liposomes and their subsequent encapsulation in a hydrocolloid matrix is a labor-intensive process that adds to the cost of the final feed. Freeze drying of microencapsulated feeds results in oxidation of the lipid component, providing a less desirable feed. Microencapsulated feeds that are stored in a dry state still have some of the same disadvantages as described for dry feeds; that is, they must still be rehydrated and manually introduced into a tank. Furthermore, the microencapsulated feeds described in the prior art have not eliminated the water pollution problems associated with the use of dry feeds.

Several types of starch and polysaccharide polymers have been proposed for use as a matrix for binding bioactive agents then mediating the controlled-release of active agents. Examples of such polymers are poly(vinylpyrrolidone), poly(vinylalcohol), poly(ethylene oxide), cellulose (and cellulose derivatives), silicone and poly(hydroxyethylmethacrylate). Polysaccharide biodegradable matrices are of interest, since the degradation of a natural product, such as starch, occurs naturally in the animal body. A combination of starch and emulsifier has also been envisioned as a method for delivery of materials to foods (Yuan 2000).

Starch and cross-linked starch obtained by treatment with reagents such as epichlorohydrin, phosphorous oxychloride, adipic anhydride, etc. are widely and safely used in the food and pharmaceutical industries with the agreement of the Food and Drug Administration. Several amylolytic enzymes naturally hydrolyze starch. Hence, $\alpha$-amylase is an endoenzyme specific to $\alpha$-(1,4)-D-glucopyranoside bonds located within polyglucose chains. The degradation product of starch amylolysis is mainly oligosaccharides, dextrins and maltose. Cross-linked and non-digestible starch has been proposed to enhance the growth of probiotic bacteria in a prebiotic fashion (Brown et al. 2002).

Starch is composed of two distinct fractions: amylose, which is a non-digested fraction containing about 4,000 glucose units, and amylopectin, which is a branched fraction containing about 100,000 glucose units. Hence, amylose and amylopectin differ not only in their chemical structures but also in their digestibility, stability in dilute aqueous solutions, gel texture, and film properties. Micellar crystals held together by hydrogen bonding between amylopectin and amylose are responsible for the integrity of starch granules. When an aqueous suspension of starch is heated to a certain temperature, the hydrogen bonding weakens and the granule swells until collapsing in a process known as "gelatinization."

The preferred conformation of amylose is a helix of variable dimension; usually it is a left-handed helix with an open core. The consequence of this helical format is that the hydroxyl group located on C6 is most reactive followed by hydroxyl groups on C-3 and finally C-2. Thus, it is possible to introduce a new substituent and chemically modify these —OH groups by, for example, an etherification process, leading to a specifically substituted amylose. The degree of substitution can be adjusted by varying the substituent to amylose ratio (mole of substituent per kg of amylose). For example, different degrees of substitution can be obtained with glycidol, ranging from 0.1 to 10.0. By choosing carefully the substituting agent and the degree of substitution, it is possible to protect the amylose from degradation and to modulate the rate of enzymatic degradation of the polymer. This opens the door to a field of research and development with commercial applications.

Numerous methods of starch gelatinization are well known in the art, including direct or indirect heating of an aqueous dispersion of starch, chemical treatment of such dispersion using strong alkali, or a combination of mechanical and heat treatment. Pre-gelatinized starch is soluble in cold water, suggesting that gelatinization of starch may not be desirable to obtain a controlled-release excipient. However, in accordance with the instant invention, it has been found that the gelatinization of high amylose starch, which can be used as a starting material, permits leaching of the amylose from the starch granules prior to a reaction with a substituted agent. This leaching of amylose provides a controlled time-release property of the instant invention.

In accordance with the instant invention, gelatinization of high amylose starch prior to the addition of substituting agent can be realized by chemical treatment using sodium hydroxide.

DISCLOSURE OF THE INVENTION

The invention provides a microparticle comprising one or more non-digestible polymer and one or more emulsifier. It may further comprise one or more bioactive agent. In an embodiment, the agent is microbound by the microparticle. The non-digestible polymer of the microparticle can include poly(vinylpyrrolidone), poly(vinylacohol), poly(ethylene oxide), cellulose, cellulose derivatives, silicone, poly(hydroxyethylmethacrylate), starch, and amylose. The bioactive agent can be, e.g., a microbe, a protein, a peptide, a nucleic acid, a hormone, a drug, an antibiotic, an enzyme, a mineral, a vitamin, a drug, an antibody, an immunogen, a microstructure, or a nanostructure. The microparticle can be provided in wet or dry form.

The invention also provides a microparticle comprising one or more non-digestible polymer and one or more emulsifier. This microparticle can comprise a polysaccharide polymer. It can also comprise one or more bioactive agent. In an embodiment, the bioactive agent is microbound by the microparticle. The bioactive agent can be, e.g., a microbe, a protein, a peptide, a nucleic acid, a hormone, a drug, an antibiotic, an enzyme, a mineral, a vitamin, a drug, an antibody, an immunogen, a microstructure, or a nanostructure. The microparticle can be provided in wet or dry form. The polymer or polypeptide can be, e.g., amylopectin, waxy maize starch, soluble starch, gluten, casein, albumin, fish meal, fish meal hydrolysate, krill meal, shrimp meal soy meal, wheat meal, cotton seed meal, or pea meal.

The invention further provides a macroparticle comprising a starch hydrocolloid or an alginate matrix comprising one or more protein. It may also provide such a macroparticle along with a microparticle as described above. This macroparticle can comprise one or more bioactive agent, which in turn can be, e.g., a microbe, a protein, a peptide, a nucleic acid, a hormone, a drug, an antibiotic, an enzyme, a mineral, a vitamin, a drug, an antibody, an immunogen, a microstructure, or a nanostructure. The bioactive agent can undergo controlled release. The macroparticle can be provided in wet or dry form. It can comprise bioattractants and/or nutrients.

The invention yet further provides a feed or feed additive comprising a microparticle which comprises a non-digestible polymer and an emulsifier. Alternatively, the feed or feed additive can comprise a microparticle with a digestible polymer, e.g., a protein polymer, and an emulsifier. These feed or feed additives can be provided to aquatic animals, such as mollusks, fish, or shrimp. They can include a bioactive agent, such as a microbe, a protein, a peptide, a nucleic acid, a hormone, a drug, an antibiotic, an enzyme, a mineral, a vitamin, a drug, an antibody, an immunogen, a microstructure, or a nanostructure. The feed or feed additive can be provided in wet or dry form.

The invention yet further provides a feed or feed additive comprising a macroparticle which comprises a non-digestible polymer and an emulsifier. It can include a bioactive agent, such as a microbe, a protein, a peptide, a nucleic acid, a hormone, a drug, an antibiotic, an enzyme, a mineral, a vitamin, a drug, an antibody, an immunogen, a microstructure, or a nanostructure. The feed or feed additives can be provided to aquatic animals, such as mollusks, fish, or shrimp. The macroparticle in the feed or feed additive can be provided in wet or dry form.

In another aspect the invention provides a method for producing a microparticle comprising a non-digestible polymer and an emulsifier. The microparticle can be used as a feed or feed additive. This method can produce a macroparticle in addition to the microparticle. In an embodiment, the macroparticle can comprise one or more of the microparticles.

The invention also provides a method for producing a microparticle comprising a digestible polymer and an emulsifier. The microparticle can be used as a feed or feed additive. The microparticle can also comprise a bioactive agent, such as a microbe, a protein, a peptide, a nucleic acid, a hormone, a drug, a antibiotic, a enzyme, a mineral, a vitamin, a drug, an antibody, an immunogen, a microstructure, and a nanostructure. The microparticle can be provided in wet or dry form. This method can produce a macroparticle that comprises a microparticle. The microparticle can be used to feed aquatic animals, such as rotifers, Artemia, mollusks, fish, and shrimp.

The invention yet further provides a method for producing a macroparticle comprising one or more digestible polymers and one or more emulsifiers. Alternatively, it provides a method for producing a macroparticle comprising a non-digestible polymer and an emulsifier. The microparticles produced by these methods can be used as a feed or feed additive for aquatic animals, such as rotifers, Artemia, mollusks, fish, and shrimp. The macroparticle can further comprise one or more bioactive agent, e.g., a microbe, protein, peptide, nucleic acid, hormone, drug, antibiotic, enzyme, mineral, vitamin, antibody, immunogen, microstructure, or nanostructure. The macroparticle can be provided in a wet or a dry form.

The invention provides a method of delivery of one or more bioactive agent comprising a microparticle with one or more non-digestible polymer and one or more emulsifier. The microparticle may further comprise one or more bioactive agent. In an embodiment, the agent is microbound by the microparticle. The non-digestible polymer of the microparticle can include poly(vinylpyrrolidone), poly(vinylacohol), poly(ethylene oxide), cellulose, cellulose derivatives, silicone, poly(hydroxyethylmethacrylate), starch, and amylose. The bioactive agent can be, e.g., a microbe, a protein, a peptide, a nucleic acid, a hormone, a drug, an antibiotic, an enzyme, a mineral, a vitamin, an antibody, an immunogen, a microstructure, or a nanostructure. The microparticle can be provided in wet or dry form.

This method of delivery can deliver bioactive agents including bacteria, yeast, viruses, *Bacillus* spp., *Bacillus licheniformis, Bacillus subtilis* strains commercially available from Chris Hansen's Biosystems, *Lactobacillus* spp., *L. bulgaricus, L. helveticus, L. plantarum, L. paracasei, L. casei, L. rhamnosus, Lactococcus* spp., *L. lactis, Alteromonas* spp., *A. media, Carnobacterium* spp., *C. divergens, Vibrio* spp., *V. alginolyticus, Pseudomonas* spp., *P. fluorescens, Streptococcus* spp., *S. lactis, S. thermophilus, Pseudoalteromonas* spp., *P. undina, Saccharomyces* spp., *S. cerevisiae, S. exiguus, Phaffia* spp., *P. rhodozoma, Pichia* spp., *P. pastoris, Kluyveromyces* spp., *K. aestuarii, K. marxianus*, and *K. yarrowii*.

This method of delivery can also deliver bioactive agents including gentamicin, tetracycline, oxytetracycline, doxycycline, ampicillin, ticarcillin, cephalothin, cephaloridine, cefotiam, cefsulodin, cefmnenoxime, cefmetazole, cefazolin, cefotaxime, cefoperazone, ceftizoxime, moxolactam, latanoxef, thienamycin, sulfazecin, and azthreonam.

This method of delivery can also deliver bioactive proteins including somatostatin, somatostatin derivatives, growth hormones, prolactin, adrenocorticotropic hormone (ACTH), melanocyte stimulating hormone (MSH), thyroid hormone releasing hormone (TRH), TRH salts, TRH derivatives, thyroid stimulating hormone (TSH), luteinizing hormone (LH), oxytocin, calcitonin, gastrin, secretin, pancreozymin, cholecystokinin, interleukins thymopoietin, thymosin, thymostimulin, thymic factors, bombesin, neurotensin, lysozyme, protein synthesis-stimulating peptides, vasoactive intestinal polypeptide (VIP), growth hormone releasing factor (GRF), and somatocrinin.

This method of delivery can deliver bioactive agents to aquatic animals, such as mollusks, fish, and shrimp. Using this method, the bioactive agents can comprise macroparticles comprising a starch hydrocolloid or an alginate matrix comprising one or more protein. The bioactive agent can undergo controlled release. The macroparticle can additionally comprise a microparticle as described above. The macroparticle can comprise a bioactive agent, e.g., a microbe, protein, peptide, nucleic acid, hormone, drug, antibiotic, enzyme, mineral, vitamin, drug, antibody, immunogen, microstructure, or nanostructure. The macroparticle can be provided in a wet or a dry form. It can comprise bioattractants or nutrients.

This method of delivery can deliver bioactive agents including bacteria, yeast, viruses, *Bacillus* spp., *Bacillus licheniformis, Bacillus subtilis* strains commercially available from Chris Hansen's Biosystems, *Lactobacillus* spp., *L. bulgaricus, L. helveticus, L. plantarum, L. paracasei, L. casei, L. rhamnosus, Lactococcus* spp., *L. lactis, Alteromonas* spp., *A. media, Carnobacterium* spp., *C. divergens, Vibrio* spp., *V. alginolyticus, Pseudomonas* spp., *P. fluorescens, Streptococcus* spp., *S. lactis, S. thermophilus, Pseudoalteromonas* spp., *P. undina, Saccharomyces* spp., *S. cerevisiae, S. exiguus, Phaffia* spp., *P. rhodozoma, Pichia* spp., *P. pastoris, Kluyveromyces* spp., *K. aestuarii, K. marxianus*, and *K. yarrowii*.

This method of delivery can also deliver bioactive proteins including somatostatin, somatostatin derivatives, growth hormones, prolactin, adrenocorticotropic hormone (ACTH), melanocyte stimulating hormone (MSH), thyroid hormone releasing hormone (TRH), TRH salts, TRH derivatives, thyroid stimulating hormone (TSH), luteinizing hormone (LH), oxytocin, calcitonin, gastrin, secretin, pancreozymin, cholecystokinin, interleukins, thymopoietin, thymosin, thymostimulin, thymic factors, bombesin, neurotensin, lysozyme chloride, protein synthesis-stimulating peptides, vasoactive intestinal polypeptide (VIP), growth hormone releasing factor (GRF), and somatocrinin.

This method of delivery can also deliver bioactive agents including gentamicin, tetracycline, oxytetracycline, doxycycline, ampicillin, ticarcillin, cephalothin, cephaloridine, cefotiam, cefsulodin, cefmenoxime, cefmetazole, cefazolin, cefotaxime, cefoperazone, ceftizoxime, moxolactam, latamoxef, thienamycin, sulfazecin, and azthreonam. This method can deliver one or more bioactive agents to aquatic animals, such as mollusks, fish, and shrimp.

BRIEF DESCRIPTION OF THE DRAWINGS

FIG. 2 is described in more detail in Example 2.

FIG. 3 is described in more detail in Example 3.

FIG. 4 is described in more detail in Example 15.

FIG. 5. The effects of probiotic feeding on shrimp survival and food conversion ratio (FCR), are shown. Feeding shrimp with *L. rhamnosus* significantly increased its survival rate after challenge with White Spot Virus. Feeding shrimp with a combination of *L. rhamnosus* and *Pseudoalteromonas undina* increased the survival rate after challenge with White Spot Virus to a greater extent than feeding with *L. rhamnosus* alone. Feeding shrimp with either *L. rhamnosus* or *Pseudoalteromonas undina* significantly decreased the food conversion ratio. Feeding shrimp with a combination of *L. rhamnosus* and *Pseudoalteromonas undina* decreased the food conversion ratio to a greater extent than feeding with either *L. rhamnosus* or *Pseudoalteromonas undina* alone. Bars designated with different letters denote significantly different values ($P<0.05$). FIG. 5 is described in more detail in Example 16.

FIG. 6 is described in more detail in Example 16.

MODES FOR CARRYING OUT THE INVENTION

SUMMARY

It is an object of the invention to provide a delivery vehicle for bioactive agents and live probiotic microbes to aquatic animals. The delivery vehicle protects the bioactive compounds and microbes from digestion and destruction in the animal stomach It is an object of the invention to provide a controlled-release delivery vehicle for bioactive agents and live probiotic microbes to aquatic animals. The controlled-release delivery vehicle gradually releases its compounds and/or microbes at their site of action along the foregut and hind gut of the animal. In order to provide predictable dissolution corresponding to the hind gut transit time of about two hours and permit reproducible release therein, the vehicle begins to dissolve within the pH range of the foregut and continues to dissolve at the pH range in the hindgut. Conditions in the hindgut can stimulate this dissolution.

It is an object of the invention to provide a method for producing a controlled-released delivery vehicle for bioactive agents and/or microbes to aquatic animals. The controlled-released delivery vehicle is provided in a form of dry or wet beadlets comprising nutrients and attractants, which are bound with soluble starch and cross-linked alginate. The bioactive agents and live probiotic microbes are bound with emulsified high amylose starch (a prebiotic compound) and embedded within the beadlets in the form of microparticles.

Bioactive agents can include, but are not limited to, drugs, vitamins, hormones, vaccines, minerals, peptides, nucleic acids, enzymes, bacteria, viruses, antibodies, nanostructures, microstructures, and immunogens. Examples of active substances include, but are not limited to, somatostatin, somatostatin derivatives, growth hormones, prolactin, adrenocorticotropic hormone (ACTH), melanocyte stimulating hormone (MSH), thyroid hormone releasing hormone (TRH) and its salts and derivatives, thyroid stimulating hormone (TSH), luteinizing hormone (LH), oxytocin, calcitonin, gastrin, secretin, pancreozymin, cholecystokinin, interleukins (e.g., IL-I, II, and III), thymopoietin, thymosin, thymostimulin, and other thymic factors, bombesin, neurotensin, lysozyme, protein synthesis-stimulating peptides, vasoactive intestinal polypeptide (VIP), and growth hormone releasing factor (e.g., GRF and somatocrinin), and etc.

Examples of antibiotics include, but are not limited to, gentamicin, tetracycline, oxytetracycline, doxycycline, ampicillin, ticarcillin, cephalothin, cephaloridine, cefotiam, cefsulodin, cefmenoxime, cefmetazole, cefazolin, cefotaxime, cefoperazone, ceftizoxime, moxolactam, latamoxef, thienamycin, sulfazecin, and azthreonam.

Examples of probiotic bacteria, include but are not limited to, *Bacillus* spp., *Bacillus licheniformis*, *Bacillus subtilis* strains commercially available from Chris Hansen's Biosystems, *Lactobacillus* spp., *L. bulgaricus*, *L. helveticus*, *L. plantarum*, *L. paracasei*, *L. casei*, *L. rhamnosus*, *Lactococcus* spp., *L. lactis*, *Bifidobacterium* spp., *B. bifidum*, *B.* sp. B420, *B. longum*, *B. lactis*, *B. johnsonii*, *B. ruminantium*, *Enterococcus* spp., *E. faecium*, *Alteromonas* spp., *A. media*, *Carnobacterium* spp., *C. divergens*, *Vibrio* spp., *V. alginolyticus*, *Pseudomonas* spp., *P. fluorescenis*, *Streptococcus* spp., *S. lactis*, *S. thermophilus*, *Pseudoalteromonas* spp., and *P. undina*. Examples of probiotic yeasts include, but are not limited to, *Saccharomyces* spp., *S. cerevisiae*, *S. exiguus*, *Phaffia* spp., *P. rhodozoma*, *Pichia* spp., *P. pastoris*, *Kluyveromyces* spp., *K. aestuarii*, *K. marxianus*, and *K. yarrowii*.

Definitions

In describing the present invention, the following terminology is used in accordance with the definitions set out below.

To "microencapsulate" a compound or component is to enclose it in a "microparticle," a spherical or irregular pellet in the size range of 20 to 150 μm, using a coating or gel, or to enclose it within a capsule. Microparticles can be made of many different compounds. In the context of the instant invention, the substance doing the "microencapsulation" is a polymeric substance that can be made up of a wide variety of materials including, but not limited to, poly(vinylpyrrolidone), poly(vinylalcohol), poly(ethylene oxide), cellulose, cellulose derivatives, starch, hemicellulose, silicone, and poly(hydroxyethylmethacrylate).

A "microbound" material is one that is enclosed and/or immobilized by being contained within a "microparticle."

"Macroparticle" and "beadlet" are used interchangeably to refer to a polymeric substance which forms a solid, semisolid, or gel that forms either regular spherical or irregularly shaped units capable of holding within them additional materials such as attractants, chemicals, microparticles, bacteria, fungi, yeast, viruses, and other useful agents. The size range of the macroparticles or beadlets ranges from about 100 μm to about 1 cm at its smallest diameter and can be up to many cm long.

A "controlled-release" delivery system is one that is manipulated to assure that the materials within a beadlet or particle are delivered intact to the desired location. Mechanisms for obtaining this controlled release are described in the specification and include manipulation of the polymeric components, inclusion of specific recognition agents in the beadlet (e.g., chitosan for the gut mucosa), pH sensitive materials, redox sensitive materials, and etc.).

A "bioattractant" is a compound that stimulates the target animal or animals to more readily consume a material. As it pertains to aquatic animals, bioattractants can be, but are not limited to, fish meal, shrimp meal, krill meal, or hydrolysates of these meals, and amino acids, such as, but not limited to, betaine, glycine, lysine, alanine, valine, proline, histidine, and taurine. For humans, bioattractants include anything that makes the materials of the instant invention more palatable or otherwise attractive, such as, but not limited to, sugars, salts, flavorings, vitamins, and oils.

Production of a Controlled-Release Delivery Vehicle

The controlled-release delivery vehicle of the instant invention is made by preparing dry or wet beadlet feed having a particle size in the range of from about 10 μm to about 10,000 μm. The beadlets can be made from a variety of components, including organic polymers, soluble and resistant starch, gums (such as acacia (gum arabic) and carrageenan), ethyl cellulose, alginate, wax, emulsifier, fat, or protein The gel is complexed or cross-linked to provide a stable particle, which can be attractive to and ingestible by a marine animal.

Preparation of Controlled-release Bioactive Agents in Microbound Particles or Microparticles Gelatinization of High Amylose Starch Granules High amylose starch (starch that contains at least 50% amylose) at a concentration of 1 to 25% w/w is dispersed in 1-5 N sodium hydroxide solution at a temperature range of 20 to 65° C. until the starch granules are fully absorbed with water and reach equilibrium. The gelatinization of high amylose starch imparts certain controlled-release properties to microparticles. In embodiments of the invention, matrix components, such as proteins and polypeptides, can be added to increase the rate of release of the bioactive agents. Examples of possible materials that can be used for modulating the rate of release include, but are not limited to, casein, albumin, soy proteins, fish meal, and krill meal. These rate-increasing components may dissolve more readily in water and gastric juices than an alternative matrix material. Upon dissolution, permeability of the particles is increased, thereby increasing access to the compounds.

Emulsification of the Gelatinized High Amylose

Under normal circumstances, the neutralization or cooling of gelatinized high amylose starch results in the reannealing of the starch grains into insoluble precipitates. This invention describes that the inclusion of an emulsifier, such as a phospholipid, prevents this reannealing of the starch grains upon cooling and neutralization This allows for the addition of bioactive or functional material to the starch at a reduced temperature, or near neutral pH, to promote the stability and/or function of the added materials.

The processes described herein can yield compositions comprising starch and emulsifier in the form of a partially or completely insoluble complex, which is stabilized by the interaction between the amylose and the emulsifier. Generally, the emulsifiers will be monoglycerides, sorbitan esters, propylene glycol esters, lecithin, polysorbates, and sucrose esters of medium and long chain saturated fatty acids (e.g., having an acyl group containing more than about 10 carbon atoms), as well as saturated fatty acids (e.g., saturated fatty acids which contain from about 12 to about 18 carbons) and unsaturated fatty acids (e.g., unsaturated fatty acids which contain from about 12 to about 22 carbons, such as oleic, linoleic, eicosapentaenoic, arachidonic and docosahexaenoic acids).

A solution of emulsifier (containing 0.5 to 12.5% w/w) can be added to the gelatinized high amylose starch in alkali solution at a temperature range of 20 to 65° C. until the starch granules are completely dissolved and a complex having a soluble nature, which is stabilized by the interaction between amylose and emulsifier, reaches equilibrium. The increased hydrophobicity of the emulsifier helps to prevent, or to delay, penetration of water or gastric juices into the matrix once formed into microparticles.

Neutralization

The alkalinity of the product is slowly reduced to a pH of approximately 7.5-8 by the addition of acid. The starch and emulsifier complex can also be co-processed with hydrocolloids, gums, polymers, modified starches, and/or combinations thereof to change the water binding capacity of the starch-emulsifier compositions. For example, xanthan gum, alginate, carrageenan, carboxymethyl cellulose, methyl cellulose, guar gum, gum arabic, locust bean gum, and/or combinations thereof can be added to the starch-emulsifier compositions at any time after neutralization, as long as the additional ingredient(s) does not dissolve the formation of the amylose-emulsifier complex. Finally, the slurry composition is allowed to cool to room temperature.

Addition of Bioactive Agents and/or Probiotic Microbes and Cross-linking Reaction A mixture comprising bioactive compounds and/or live microbes or viable spores are dissolved into the slurry, and the composition can be optionally dried to produce a powder by a number of methods generally recognized for this purpose, e.g., low temperature spray drying, belt drying, freeze drying, drum drying, or flash drying. For example, the dispersion can be atomized and cross-linked in a calcium-chloride bath. The wet microparticles can be refrigerated at approximately 4° C. until use, or they can be dried and stored at room temperature. Dried microparticles can be rehydrated with water or another aqueous medium prior to use, or allowed to rehydrate upon delivery.

Preparation of Beadlets or Macroparticles

Hydrocolloid Formation

Waxy maize starch (comprising at least 50% amylopectin) containing 1 to 25% w/w of bioactive or functional agent is dispersed in water at a temperature range of 20 to 65° C. until the starch is completely dissolved. The starch slurry is co-processed with 0.5-12.5% w/w xanthan gum, alginate, carrageenan, carboxymethyl cellulose, methylcellulose, guar gum, gum arabic, locust bean gum, and/or combinations thereof. Finally, the hydrocolloid slurry composition is allowed to cool to room temperature.

Addition of Proteins Nutrients, and Attractants

Attractants, such as, but not limited to, fish, krill, shrimp, or crab meal hydrolysates, or any combination of aquatic animal meal hydrolysates containing 3-30% w/w is dissolved into the hydrocolloid as well as 1-5% w/w betaine and glycine+alanine mixture as attractants. The addition of protein or polypeptide to the beadlets provides sites and pores that can be opened by GI proteases or other enzymes, which allows the aquatic animal to partially digest the feed. Other nutrients or enzymes such as, but not limited to, amino and fatty acids, sugars, polysaccharides, minerals, vitamins, proteases, lipases, and amylases can be added to the hydrocolloid slurry.

Addition of the Controlled-release Microparticles Containing One or Several Bioactive Agents and/or Probiotic Microbes Effective concentrations, determined empirically, of wet and/or dry microparticle preparation(s) can be added to the hydrocolloid slurry and mixed thoroughly.

Cross-linking Reaction and Beadlet Preparation

The hydrocolloid slurry can be optionally dried and pelleted into various sizes ranging from about 100 μm to about 10,000 μm and stored at room temperature, or dropped through various sizes of tubes ranging from about 100 μm to about 10,000 μm and cross-linked in a calcium-chloride bath, dip, or spray. Any type of preservative such as, but not limited to, propylene glycol, glycerol, calcium chloride, or BHT, can be added and the wet beadlets refrigerated at 4° C. until use. An additional step of drying the beadlets can be performed to produce a dry product

EXAMPLES

Certain embodiments of the invention will now be described in more detail through the following Examples. The Examples are intended solely to aid in more fully describing selected embodiments of the invention and should not be considered to limit the scope of the invention in any way.

Example 1

Production of Controlled-released Microparticles Containing the Probiotic Microbes *Lactobacillus rhamnosus*

Figure 1:
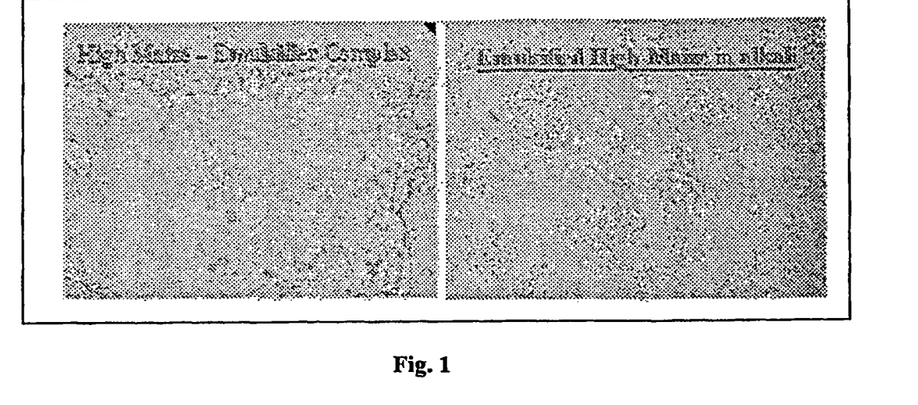
FIG. 1. The effect of the addition of lecithin to gelatinized high amylose starch granules in alkali solution is shown in two comparative micrographs. The left panel shows a gelatinized granule at the beginning of the complexing process, which is detailed further in Example 1, and the right panel shows dissolved granules and the resulting complex formation of lecithin with the starch polymers.

Four grams of high amylose starch (70% amylose; Hylon VII, National Starch and Chemical, Bridgewater, N.J.) was dissolved in 1 N sodium hydroxide at 50° C. (FIG. 1, left panel). Two grams of powdered egg lecithin (Archer-Daniels-Midland Co., Decatur, Ill.) was added to the alkali slurry and allowed to complex with the amylose for 30 min (FIG. 1, right panel). As shown in FIG. 1, a physical difference is observed as the starch granules become hydrated (gelatinized). The alkali complex slurry was then neutralized to pH 7.5 with hydrochloric acid. Two grams of alginic acid was then dissolved in the hydrated starch slurry then, once dissolved, allowed to cool to room temperature. Twenty grams of *L. rhamnosus* (LCS-742, Morinaga Milk Industry Co., LTD., Kanagawa, Japan) were added to the cooled and neutralized starch/alginate slurry. The slurry was then atomized using a Graco 190ES paint sprayer into a 5% w/w calcium chloride and 1% w/w sodium chloride bath to form nicroparficles in a size range between about 10 μm and about 100 μm. The microparticles were washed with tap water on a fine mesh screen, and kept refrigerated at 4° C. until use. The composition of the microparticles is provided in Table 1.

TABLE 1

| Microparticle Composition (g dry weight/100 g) | |
| --- | --- |
| High amylose (70% amylose) | 4 g |
| Egg lecithin | 2 g |
| Alginic acid | 2 g |
| L. rhamnosus | 20 g |
| Water | 72 g |

Example 2

Viability of Lactobacillus rhamnosus Bacteria in Beadlets

Figure 2:
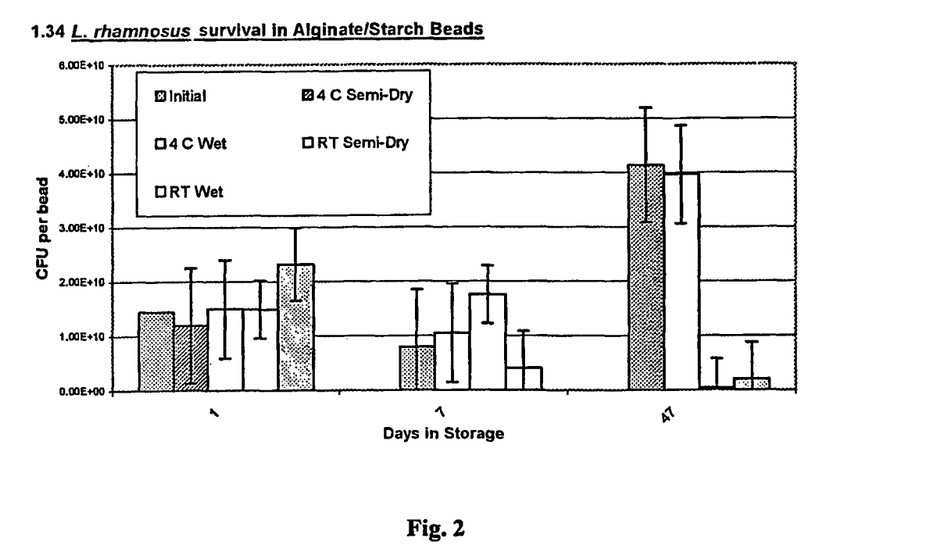
FIG. 2. The viability of *Lactobacillus rhamnosus* bacteria encapsulated in beadlets, is presented as the number of colony forming units per bead following 1, 7, or 47 days in storage.

Beadlets were prepared as in Example 1 and left as semi-dry (i.e., the beadlets were drained of water, but the beadlets were not further dried) were tested for the viability of the microbound bacteria over time at 4° C. and at room temperature. Beadlets were tested by removing ten beadlets from the batch to a sterile Beadbeater tube containing ⅓ volume of sterile 5 mm glass beads. Sterile water (1 mL) was added to fill the tube and the tube was processed in the Beadbeater for up to three 40-second pulses to disrupt the beads. This material was serially diluted into sterile water blanks and spread plated on Lactobacillus MRS Agar (Difco). Plates were incubated at 30° C. for 2-3 days and the number of L. rhamnosus colonies counted. The survival rates of the bacteria are shown in FIG. 2. The bacterial viability decreased over time during the room temperature storage treatment but increased during the 4° C. storage treatment versus the initial bacterial counts.

Example 3

Production of Controlled-release Microparticles Containing an Infectious Pancreatic Necrosis Virus (IPNV) Vaccine A complex slurry was prepared as described in Example 1 and adjusted to pH 7.5 with HCl. Baker's yeast (20 g wet weight Saccharomyces cerevisiae) expressing IPNV particles was then added to the cool and neutralized slurry (produced at Advanced BioNutrition Corp.). The slurry was then atomized into 5% w/w calcium chloride and 1% w/w sodium chloride bath to form microparticles in a size range between about 10 μm and about 100 μm. The microparticles were washed with tap water on a fine mesh screen and kept refrigerated at 4° C. until use. The composition of the microparticles is provided in Table 2.

TABLE 2

| Microparticle Composition (g dry weight/100 g) | |
| --- | --- |
| High amylose (70% amylose) | 4 g |

TABLE 2-continued

| Microparticle Composition (g dry weight/100 g) | |
| --- | --- |
| Egg lecithin | 2 g |
| Alginic acid | 2 g |
| IPNV Yeast | 20 g |
| Water | 72 g |

Example 4

Figure 3:
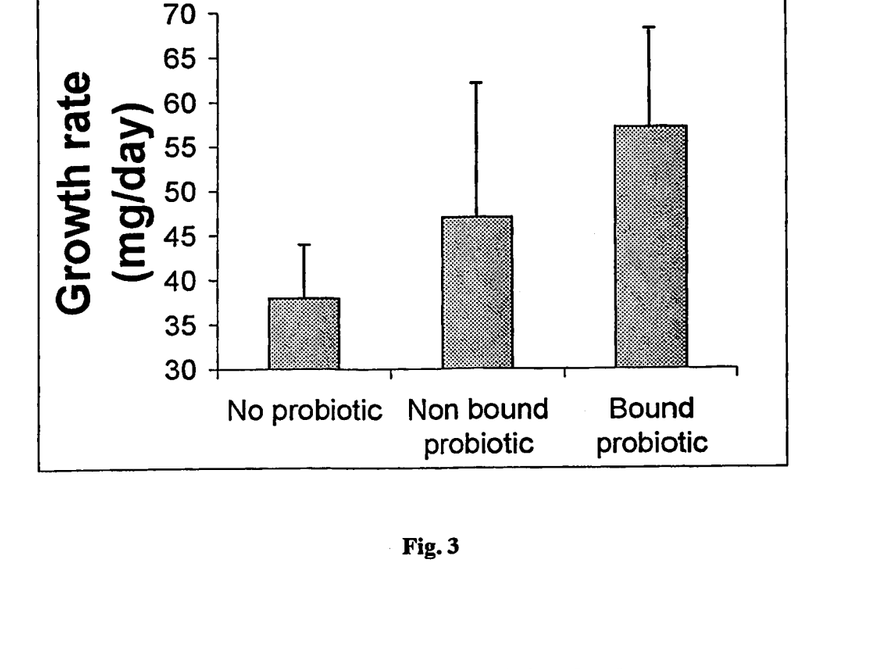
FIG. 3. The comparative effect of *L. rhamnosus* delivery in a microbound form and a non-microbound form on the daily growth rate of juvenile hybrid striped bass is shown. Growth rates are presented as the mean ±S.E, n=9.
Figure 4:
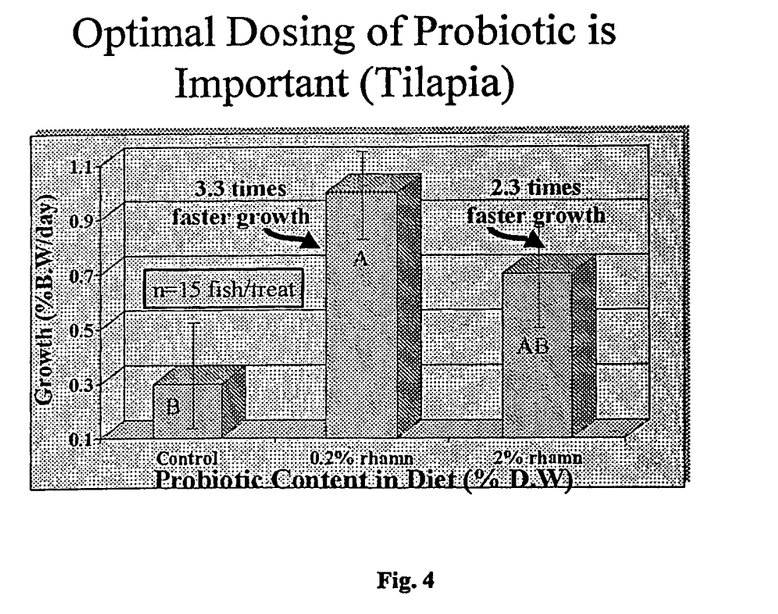
FIG. 4. The effect of probiotic dosing ranges (0-2%) on the growth rate of tilapia fry is shown as the growth in body weight per day. Bars designated "A" denote a growth rate significantly different from bars designated "B" ($P<0.05$, n=15).

Delivery of the Probiotic Bacterium L. rhamnosus to Hybrid Striped Bass Fry in Beadlets In addition to a standard commercial diet, hybrid striped bass juveniles (1-2 g) were fed at 0.2% body weight/day with moist beadlets containing live L. rhamnosus, either microbound or not microbound, with high amylose complex The entire digestive tract was then removed from the fish and the stomach dissected away. One gut was placed in a sterile Beadbeater tube containing ⅓ volume of sterile 5 mm glass beads. Sterile water (1 mL) was added to fill the tube and the tube was processed in the Beadbeater for up to three 40-second pulses to disrupt the gut tissue. This material was serially diluted into sterile water blanks and spread plated on Lactobacillus MRS Agar (Difco). Plates were incubated at 30° C. for 2-3 days and the L. Rhamnosus colonies counted. As shown in Table 3, feeding the fish with beadlets containing microbound L. rhamnosus resulted in intestinal colonization levels exceeding those obtained with non-microbound bacteria ($10^4$ cfu/gut in fish fed microbound L. rhamnosus vs. $10^2$ cfu/gut in fish fed non microbound bacteria). Intestinal colonization was evident even after 10 days of washout with a standard diet. The growth rates of the fish are shown in FIG. 3. Fish fed beadlets containing microbound L. rhamnosus attained a growth rate over 50% higher than fish fed with beadlets that did not contain L. rhamnosus.

TABLE 3

Effect of Delivery Form on Gut Colonization (cfu/gut) of Hybrid Striped Bass with L. Rhamnosus

| Treatment | Beadlet Count | Intestinal Count (after 21 days of feeding) | Intestinal Count (after 10 days of washout) |
| --- | --- | --- | --- |
| No probiotic | 0 | 0 | 0 |
| Non microbound probiotic | $10^2$ cfu/day | $10^2$ cfu/gut | $10^1$ cfu/gut |
| Microbound probiotic | $10^1$ cfu/day | $10^4$ cfu/gut | $10^2$ cfu/gut |

Example 5

Production of Controlled-release Microparticles Containing GnRH Reproductive Hormones A complex slurry is prepared as described in Example 1 containing 4 g high amylose starch, 3 g egg lecithin, 2 g alginic acid, and 91 g water, and adjusted to pH 7.5. A solution containing a synthetic GnRH analog (Ovaprim, Syndel International Inc., Vancouver, BC. Canada) is then added to the cool and neutralized slurry. The slurry is then atomized into a 5% w/w calcium chloride and 1% w/w sodium chloride bath to form microparticles in a size range between about 10 μm and about 100 μm. The microparticles are washed with tap water on a fine mesh screen and kept refrigerated at 4° C. until use. The composition of the microparticles is provided in Table 4.

TABLE 4

| Microparticle Composition (g dry weight/100 g) | |
|---|---|
| High amylose (70% amylose) | 4 g |
| Egg lecithin | 3 g |
| Alginic acid | 2 g |
| Ovaprim | 2 mg |
| Water | 91 g |

Example 6

Production of Beadlets Containing Controlled-release Microparticles with IPNV Vaccine and a Probiotic Microbe Three grams of waxy maize starch (Ultra-Sperse M, National Starch and Chemical, Bridgewater, N.J.) are dissolved in 45 g of distilled water at 50° C. Two grams of alginate are then dissolved in the slurry and allowed to cool to room temperature. Ten grams of a fishmeal hydrolysate and attractant preparation (Aqua Savor, Bentoli, Inc., Homestead, Fla.) are dissolved into the cool hydrocolloid and equal amounts (20 g or each) of probiotic microparticles and IPNV vaccine containing yeast microparticles as described in Examples 1 and 2, respectively, are added to the hydrocolloid. The hydrocolloid slurry is then added dropwise into 5% w/w calcium chloride and 1% w/w sodium chloride bath using a peristaltic pump with a 5 mm tube diameter. The beadlets are collected on a screen washed thoroughly under tap water and stored at room temperature in brine solution. The composition of the microparticles is provided in Table 5.

TABLE 5

| Beadlet Composition (g dry weight/100 g) | |
|---|---|
| Waxy maize (70% amylopectin) | 3 g |
| Alginic acid | 2 g |
| Aqua Savor | 10 g |
| Probiotic microparticles | 20 g (wet weight) |
| IPNV yeast microparticles | 20 g (wet weight) |
| Water | 45 g |

Example 7

Feeding of Trout Fish with Probiotic/IPNV Vaccine Beadlets

Trout fry at ca. 100 g size are stocked at 30 kg per $m^3$ of fresh water at 15° C. Water quality is maintained by rapidly exchanging the tank water through mechanical and biofiltration systems. Fish are fed 4 times daily a total ration of 2% body weight on a commercial feed and 2% (wet weight) controlled-released beadlets as described in Example 3 for 21 days. Daily growth rates are calculated according to the following formula:

(Growth Rate=(Final average fish weight)−(Initial average weight)/(Days of growth)

Food conversion ratio (FCR) is calculated according to the following formula:

FCR=((Total food given)/(Total fish final biomass))−(Total fish initial biomass in grans).

Blood samples are taken for analysis for antibodies specific to IPNV and for gut microflora analysis to quantitate the probionts present.

Example 8

Production of Beadlets Containing Controlled-released Microparticles Having GnRH Synthetic Analog Hydrocolloid was produced as described in Example 6 and GnRH microparticles that were prepared as described in Examples 5 were added to the cooled hydrocolloid solution The hydrocolloid slurry was then added dropwise into 5% w/w calcium chloride and 1% w/w sodium chloride bath using a peristaltic pump and a 5 mm tube diameter. The beadlets were collected on a screen, washed thoroughly under tap water, and stored at room temperature in brine solution. The composition of the microparticles is provided in Table 6.

TABLE 6

| Beadlet Composition (g dry weight/100 g) | |
|---|---|
| Waxy maize (70% amylopectin) | 3 g |
| Alginic acid | 2 g |
| Aqua Savor | 10 g |
| GnRH Microparticles | 20 g (wet weight) |
| Water | 65 g |

Example 9

Feeding of Trout Fish with GnRH Beadlets

Trout broodstock are stocked at 10 kg per $m^3$ of freshwater and at temperature of 10° C. Water quality is maintained by rapidly exchanging the tank 4 water through mechanical and biofiltration systems. Fish are fed 4 times daily a total ration of 2% body weight on a commercial feed and 2% (wet weight) controlled-released beadlets as described in Example 3 for 14 days. Blood samples are taken for GnRH profile analysis and compared with fish fed only a standard commercial feed.

Example 10

Feeding of Shrimp (*Penaeus vannamei*) with a Probiotic Mixture

Shrimp fry at ca. 10 g size are stocked at 10 kg per $m^3$ of seawater and at temperature of 28° C. Water quality is maintained by rapidly exchanging the tank water through mechanical and biofiltration systems. Shrimp are fed a standard pelleted feed 4 times daily a total ration of 2% body weight and pellet size adjusted to fit the mouth opening of the growing shrimp. In addition to the standard feed, shrimp are also fed with 0.2% body weight of moist beadlets containing a mixture of equal quantities of microbound *L. rhamnosus* and *Pseudoalteromonas undina* (DSMZ 6065, Deutsche Sammlung von Mikroorganismen und Zellk-ulturen GmbH). Microbound bacteria are prepared as described in Example 1. The experiment is terminated when shrimp reach an average commercial size of 40 g. Daily growth rate and food conversion ratio is calculated as described in Example 7.

A sample of 20 shrimp are placed in a contained tank and infected with white spot virus (WSV) and survival recorded over a 2-week period following the infection.

Example 11

Figure 5:
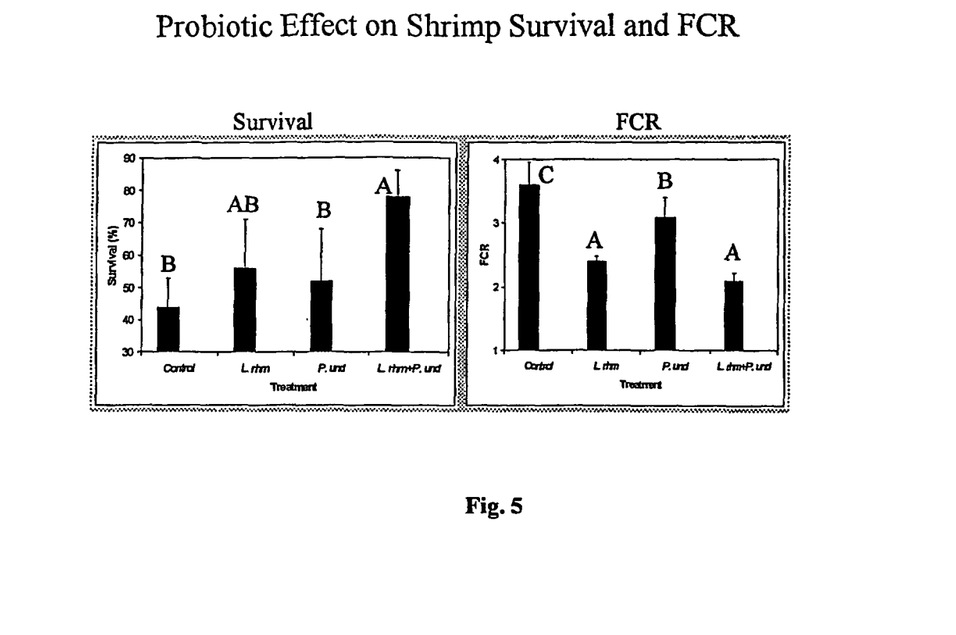

Production of Controlled-release Microparticles Containing a Cat Virus (Feline Herpes Virus 1; FHV1) Vaccine A complex slurry is prepared as described in Example 1 using 4 g high amylose starch, 2 g egg lecithin, 2 g alginic acid, and 72 g water, then adjusted to pH 7.5 with HCl. Twenty grams wet weight of Baker's yeast (*Saccharomyces cerevisiae*) expressing FHV1 particles is then added to the cool and neutralized slurry. The slurry is then atomized into a 5% w/w calcium chloride and 1% w/w sodium chloride bath to form microparlicles in a size range between 10 μm and 100 μm. The microparticles are washed with tap water on a fine mesh screen, freeze-dried, and kept as dry powder until use. The composition of the microparticles is provided in Table 7.

TABLE 7

| Microparticle Composition (g dry weight/100 g) | |
|---|---|
| High amylose (70% amylose) | 4 g |
| Egg lecithin | 2 g |
| Alginic acid | 2 g |
| FHV1-containing yeast | 20 g |
| Water | 72 g |

Example 12

Feeding Cats with Extruded Feeds Top-coated with FHV1 Vaccine Beadlets

A standard commercial pelleted cat feed is top coated with a slurry of 1% alginate and 20% microparticles as described in Example 11, using a paint spray gun. The top-coated pellets are then dried overnight at 40° C. Feeds containing the FHV1 are fed to 10 cats for 1 week followed by 2 weeks of standard feed and an additional 1 week of a boosting dose with the vaccine top coated feed. Blood samples are taken after 1 month from the initiation of the experiment and analyzed to determine the antibody titer against FHV1.

Example 13

Bioactive Compound Delivery to Humans with Beadlets

Particles are prepared according to the methods described in Example 1, and the procedures are validated to conform to GMP (Good Manufacturing Procedures) to allow use as a delivery device in humans. Standardized nutritional supplements can be delivered in this manner to humans. Powdered *Echinacea purpurea* extract from the aerial parts of the plant that have been standardized to 4% phenolic compounds is added to a standardized dosage rate of 1 mg of phenolic compound/g of beadlet. Masking agents or flavoring such as vanillin is used to make the beadlets more palatable. The beadlets are then made in a range of 200 to 300 μm diameter and spray dried. These spray dried beads are then used as a top coating for cereal delivering 1 mg of the-phenolic compound to the human per treatment dose.

Example 14

Oral Delivery of Insulin

Peroral insulin delivery has presented a challenge, since insulin is rapidly degraded in the stomach Taking insulin by mouth would be a great relief to diabetics; however, most current approaches use injection due to the cost of insulin and the large doses required for oral delivery. Companies, such as Nobex and GlaxoSmithKline, are currently making approaches to deliver oral insulin by chemical modification of the insulin (e.g., by attaching polyethylene glycol to the insulin). The instant invention provides another alternative, namely, delivery in alginate/starch beads in a microbound format.

Microparticles are made using techniques described in the above examples using the formulation in Table 8 and $CaCl_2$ polymerization. Beadlets are formed that contain between 11 and 14 U per gram wet weight. The particle size is adjusted to between about 0.1 and about 0.2 mm and the beads are spray dried. Spray dried beads are then rehydrated prior to use in water for approximately one minute and consumed by drinking. Concentration is varied from 880 to 1140 to provide a dose of 11-14 U allowing for differences in patient size while still delivering in a single gram dose.

TABLE 8

| Microparticle composition (g dry weight/100 g) | |
|---|---|
| High amylose (70% amylose) | 4 g |
| Egg lecithin | 2 g |
| Alginic acid | 2 g |
| Insulin (Nph) | 880-1140 Units |
| Lemon oil | 1 g |
| Water | 72 g |

Example 15

Dose Response of the Probiotic Bacterium *Lactobacillus rhamnosus* Fed to Tilapia Fry in Beadlets In addition to a standard commercial diet, tilapia juveniles (1-2 g) were fed at 0, 0.2, and 2% of their body weight/day with moist beadlets containing live *L. rhamnosus* micro-bound with high amylose complex prepared as described in Example 1. The growth rates of the fish are shown in FIG. 4. Fish fed beadlets containing 0.2% micro-bound *L. rhamnosus* attained a 3.3 times higher growth rate than fish fed with control beadlets that did not contain *L. rhamnosus*. Increasing the dosage of bacteria did not provide additional growth, and treatment with 2% *L. rhamnosus* did not produce an effect on growth that was significantly different from the control diet.

Example 16

Feeding Pacific White Shrimp (*Penaeus vannamei*) with a Probiotic Mixture: Effect on Challenge with White Spot Virus Shrimp fry at ca. 10 g size were stocked at 10 kg per $m^3$ of seawater and at temperature of 28° C. Water quality was maintained by rapidly exchanging the tank water through mechanical and biofiltration systems. Shrimp were fed a standard pelleted feed 4 times daily a total ration of 2% body weight and the pellet size was adjusted to fit the mouth opening of the growing shrimp. In addition to the standard feed, shrimp were also fed with 0.2% body weight of moist beadlets containing a mixture of equal quantities of microbound *L. rhamnosus* and *Pseudoalteromonas undina* (DSMZ 6065, Deutsche Sammlung von Mikroorganismen und Zellkulturen GmbH). Microbound bacteria were prepared as described in Example 1. The experiment was terminated when the shrimp reached an average commercial size of 40 g. Shrimp survival and FCR are presented in FIG. 5. Daily growth rate and food conversion ratio were calculated as described in Example 7. The inclusion of probionts, either *L. rhamnosus* or a combination of *L. rhamnosus* and *P. undina*,resulted in an increase in the survival rate of the shrimp and a decrease in their FCR.

Figure 6:
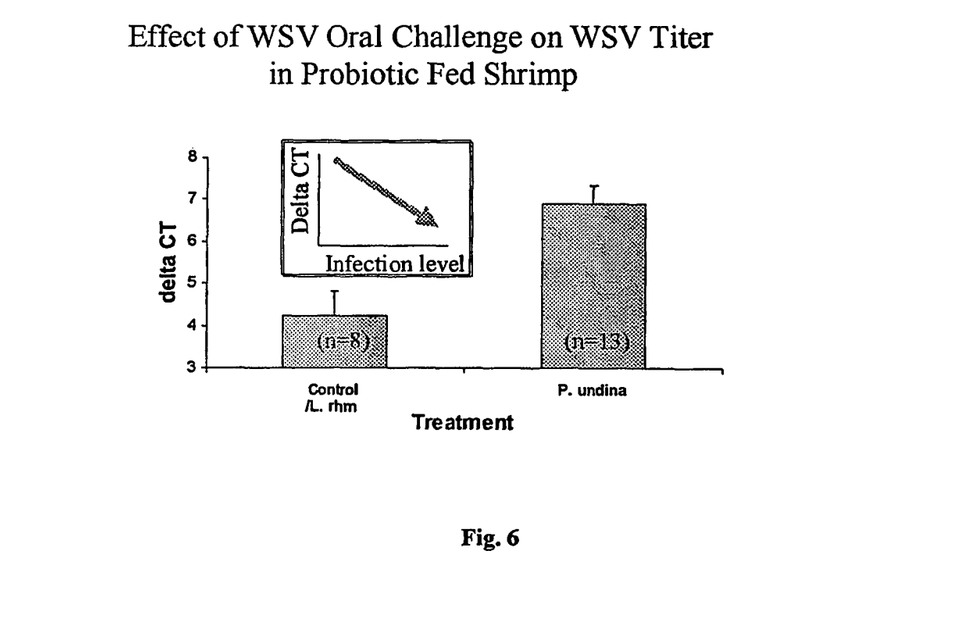
FIG. 6. The effect of an oral challenge with White Spot Virus on the WSV viral load is shown. Viral load was measured by WSV-specific PCR analysis of pleopod samples by the method of Dhar et al., 2002. A lower delta cycle threshold ($C_T$) value indicates a higher viral load. *Pseudoalteromons undina* significantly decreased the viral load of the shrimp that consumed the microencapsulated probiont.

A sample of 20 shrimp were placed in a contained tank and orally infected with white spot virus (WSV) while being maintained on a feed supplemented with microencapsulated *P. undina*. After a 2 week incubation period, the viral load was determined using real time RT-PCR by the method of Dhar (Dhar et al. 2002). A linear relationship exists between input DNA and the cycle threshold value ($C_T$). As the virus is repressed, the $C_T$ value is increased. The *P. undina* feed repressed growth of the WSV, while the control and *L. rhamnosus* feeds did not inhibit the virus, as shown in FIG. 6.

Example 17

Sample Production Method for Microencapsulated Probiotic Organisms

A probiotic microencapsulation formulation is herein described to produce 1 kg at a 20% bacterial load. The procedure can be modified to adjust the bacterial load using standard methods. For example, the water content of some probionts, e.g., *P. undina* paste, may be sufficiently high that only a maximum loading of less than 20% can be achieved. The weight of all the ingredients should be calculated before beginning, in order to determine the appropriate amount of water in the starting material.

Distilled water (726 ml) is added to a 1 liter glass beaker on a stir/heat plate and the speed of the stir bar adjusted to maximum with care taken to avoid splashing. Ten grams sodium hydroxide is added and allowed to dissolve. Fourteen grams Hi-Maize starch (Hylon VII—National Starch) is added, followed by fourteen grams soy lecithin (Epikuron 100P—Degussa). The thermostat is adjusted to achieve a liquid temperature of approximately 50° C. and the mixture stirred for approximately 2 hours. The appearance of the mixture will change from opaque to semi transparent and slightly yellow when the reaction is complete. Microscopic inspection can verify that the starch granules are gelatinized. The mixture is allowed to cool and adjusted to a pH of between about 7.3 and about 7.8 with the addition of approximately 15 ml concentrated HCl. The mixture will lighten in color and become opaque when the pH reaches approximately 8.5-8.0.

Ten grams sodium alginate (T-500, food grade, Multi-Kem Corp.) is slowly added to this mixture. A high speed mixer is used for approximately 1 hour or until the alginate granules are completely dissolved. When encapsulating unwashed *P. undina*, 5 g sodium hexametaphosphate (practical grade) are added to the mixture before adding the alginate.

The probiont, e.g., bacteria in dry, e.g., dehydrated, or paste form, is then added to the mixture and mixed thoroughly until homogeneous. When using a paste, determine the moisture content per viable cell using standard methods. For example, 200 g lyophilized *Lactobacillus*, or an amount of *undina* paste equivalent to 200 g solids, based on moisture analysis, can be encapsulated by this method. The mixture is ready to be sprayed at this point. Spraying should be done immediately after the bacteria are added to the encapsulation mixture The weight of the microencapsulated mixture prior to spraying and cross-linking is directly proportional to the weight of the finished product. No water is gained or lost in the process. When the probiont is in the form of a paste, the moisture/solids content can be used to determine the appropriate amount of water in the starting material. The contribution of water in the paste is factored into the recipe and considered as contributing to the amount of water added to the mixture.

Adjustments may be required in the ionic composition of the wash solutions and procedures. For example, when washing *undina* paste, excess chloride ions in the paste may dictate the addition of sodium hexametaphosphate to the mixture at an amount equivalent to approximately 50% of the weight of the alginate.

Example 18

Spray Gelling of Alginate Materials in a Starch Matrix

Several feeds of alginates in starch matrix were gelled by spraying the feed into a bath of calcium chloride (Dowflake, process grade, Dow). The materials formed gelled particles that were recovered from the bath by sifting. The feed was charged into a 30 gallon tank and pumped using a Moyno progressing cavity pump into a Shlick two fluid nozzle spraying into a second 30 gallon tank. The second tank was tilled with a bath of calcium chloride in water. At the end of each run the bath was drained through sieves to recover the product. Calcium chloride loads were 3-5%. Nozzle sizes and atomizing conditions were selected by Niro to obtain good atomization. No attempt was made to maximize throughput or to correlate spray conditions to particle sizes. The objective was to produce material for field trials.

Figure 7:
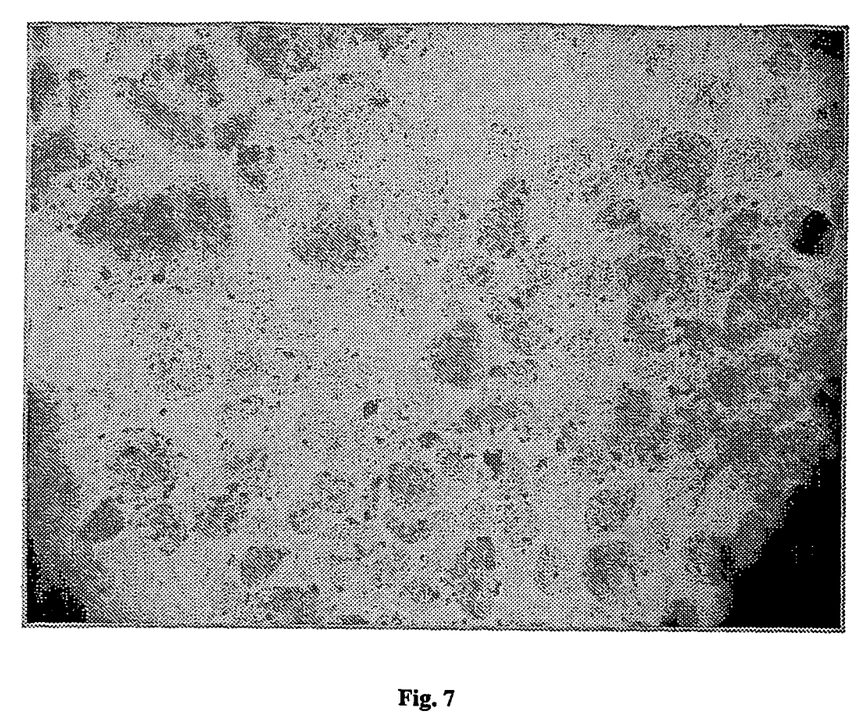
FIG. 7. A micrograph of the alginate/starch beads, produced as further described in Example 18, are shown.

A number of different (0.5 to 1.3) nozzle orifices were utilized in these runs and provided particles of various sizes. The size can be manipulated by the size of the orifice attached to the Shlick fluid sprayer. Manipulation of the atomizing air rate was used also as a way of manipulating the size the particle (increasing the air flow decreases the size of the particle). Airflow rate was adjusted according to the viscosity of the feed (which increased on addition of the two probionts utilized (*L. rhamnosus*<*P. undina*). Generally, a higher viscosity requires a larger nozzle diameter to attain the same sized beads. Beads were made and provided as shown in FIG. 7 containing *L. rhamnosus, L. rhamnosus*, and *P. undina*, and feeds without either bacterium

REFERENCES

Amidon G, Leesman G (1993) Pulsatile drug delivery system. In: U.S. Pat. No. 5,229,131. University of Michigan, USA.

Brown I, Conway P, Evans A, Henriksson K, McNaught K, Wang X (2002) Alterations of microbial populations in the gastrointestinal tract. In: U.S. Pat. No. 6,348,452 B1.

Univ of New South Wales, Burns Philip & Co., CSIRO, Gist-Brocades Aust, Goodman Fielder Ingredients Ltd., USA Dhar A K, Roux M M, Klimpel K R (2002) Quantitative assay for measuring the Taura syndrome virus and yellow head virus load in shrimp by real-time RT-PCR using SYBR Green chemistry. J. Virol. Methods 104:69-82.

Hayward J, Levine D, Simon S (1987) Microcapsules. In: PCT Publ WO8701587.

Levine D, Sanford S, Hayward J (1987) Microcapsules. In: European Patent EP0237542.

Muhammad N, Boisvert W, Harris M, Weiss J (1993) Sustained release formulations. In: U.S. Pat. No. 5,188,836. Warner-Lambert Company, USA.

Sache E, Bertrand H (1980) Liposomes containing heparin and a process for obtaining them. In: U.S. Pat. No. 4,239,754. Choay, S. A.

van Lengerich B (2001) Embedding and encapsulation of controlled release particles. In: U.S. Pat. No. 6,190,591. General Mills, USA.

Villamar D F, Langdon C (1993) Delivery of dietary components to larval shrimp (*Penaeus vannamei*) by means of complex microcapsules. Marine Biol. 115:635-642.

Yuan C (2000) Starch emulsifier compositon and methods of making. In: U.S. Pat. No. 6,017,388. Opta Food Ingredients, Inc., USA.

I claim:

1. A macroparticle comprising a microparticle and a matrix, wherein the microparticle is embedded in the matrix, wherein the microparticle comprises a bioactive agent, a high amylose starch comprising at least 50% w/w amylose, an emulsifier and an additional ingredient, wherein the additional ingredient is selected from the group consisting of alginate, carrageenan, and combination thereof, and wherein the additional ingredient is crosslinked with crosslinking agent calcium chloride, and wherein the matrix comprises a starch hydrocolloid comprising at least 50% w/w/ amylopectin, and a crosslinked alginate.

2. The macroparticle of claim 1, wherein the microparticle is prepared by a method comprising:
    (a) gelatinizing the high amylose starch in an alkali solution, whereby the high amylose starch are gelatinized;
    (b) emulsifying the gelatinized high amylose starch with the emulsifier to form an emulsion comprising a starch-emulsifier complex;
    (c) neutralizing pH of the emulsion;
    (d) adding the bioactive agent and the additional ingredient to the pH-neutralized emulsion, wherein the additional ingredient does not dissolve the starch-emulsifier complex, whereby a dispersion is obtained;
    (e) atomizing the dispersion into a solution containing calcium chloride; and
    (f) cross-linking the additional ingredient in the atomized dispersion with the calcium chloride, whereby the microparticle is formed.

3. The macroparticle of claim 1, wherein the bioactive agent is selected from the group consisting of microbes, proteins, peptides, nucleic acids, hormones, drugs, antibiotics, enzymes, minerals, vitamins, antibodies, and immunogens.

4. The macroparticle of claim 3, wherein the bioactive agent is a microbe selected from the group consisting of *Bacillus* spp., *Bacillus licheniformis*, *Bacillus subtilis*, *Lactobacillus* spp., *L. bulgaricus*, *L. helveticus*, *L. plantarum*, *L. paracasei*, *L. casei*, *L. rhamnosus*, *Lactococcus* spp., *L. lactis*, *Alteromonas* spp., *A. media*, *Camobacterium* spp., *C. divergens*, *Vibrio* spp., *V. alginolyticus*, *Pseudomonas* spp., *P. fluorescens*, *Streptococcus* spp., *S. lactis*, *S. thermophilus*, *Pseudoalteromonas* spp., *P. undina*, *Saccharomyces* spp., *S. cerevisiae*, *S. exiguus*, *Phaffia* spp., *P. rhodozoma*, *Pichia* spp., *P. pastoris*, *Kluyveromyces* spp., *K. aestuarii*, *K. marxianus*, and *K. yarrowii*.

5. The macroparticle of claim 3, wherein the bioactive agent is a protein selected from the group consisting of somatostatin, growth hormones, prolactin, adrenocorticotropic hormone (ACTH), melanocyte stimulating hormone (MSH), thyroid hormone releasing hormone (TRH), TRH salts, thyroid stimulating hormone (TSH), luteinizing hormone (LH), oxytocin, calcitonin, gastrin, secretin, pancreozymin, cholecystokinin, interleukins, thymopoietin, thymosin, thymostimulin, thymic factors, bombesin, neurotensin, lysozyme, growth hormone releasing factor (GRP). and somatocrinin.

6. The macroparticle of claim 1, wherein the bioactive agent is selected from the group consisting of gentamicin, tetracycline, oxytetracycline, doxycycline, ampicillin, ticarcillin, cephalothin, cephaloridine, cefotiam, cefsulodin, cefmenoxime, cefrnetazole, cefazolin, cefotaxime, cefoperazone, ceftizoxime, moxolactam, latamoxef, thienamycin, sulfazecin, and azthreonam.

7. The macroparticle of claim 1, wherein the matrix comprises a nutrient.

8. The macroparticle of claim 1, wherein the bioactive agent is selected from the group consisting of a protein, and polypeptide.

9. The macroparticle of claim 1, wherein the bioactive agent is selected from the group consisting of casein, albumin, soy proteins, fish meal, and krill meal.

10. The macroparticle of claim 1, wherein the emulsifier is selected from the group consisting of monoglycerides, sorbitan esters, lecithin, polysorbates, and sucrose esters of medium or long chain saturated fatty acids, and unsaturated fatty acids.

11. The macroparticle of claim 2, wherein the starch-emulsifier complex has a weight ratio of the emulsifier to the high amylose starch from 1:5 to 5:1.

12. The macroparticle of claim, 2, wherein the starch-emulsifier complex has a weight ratio of the emulsifier to the high amylose starch from 1:2 to 2:1.

13. The macroparticle of claim 2, wherein the starch-emulsifier complex has a weight ratio of the emulsifier to the high amylose starch of 2:1.

14. The macroparticle of claim 2, wherein the pH is neutralized to 7.5-8.0.

15. The macroparticle of claim 1, wherein the macroparticle is in the form of a dry powder.

16. The macroparticle of claim 15, wherein the wherein the macroparticle is formed by low temperature spray drying, freeze drying, drum drying or flash drying.

17. A method for delivering a bioactive agent to an aquatic animal, comprising feeding the macroparticle of claim 1 to the aquatic animal.

18. The method of claim 17, wherein the aquatic animal is selected from the group consisting of mollusks, fish, and shrimp.

19. A feed, food, feed additive, or food additive comprising the macroparticle of claim 1.

20. The macroparticle of claim 1, wherein the additional ingredient is alginate.

21. The macroparticle of claim 1, wherein the microparticle has a particle size in the range of 10 μm to 150 μm.

* * * * *